United States Patent [19]
Cutler

[11] Patent Number: 5,945,097
[45] Date of Patent: Aug. 31, 1999

[54] METHOD FOR LOWERING CHOLESTEROL LEVELS WITH INTERLEUKIN-10

[75] Inventor: David Cutler, Morristown, N.J.

[73] Assignee: Schering Corporation, Kenilworth, N.J.

[21] Appl. No.: 08/924,855

[22] Filed: Sep. 5, 1997

Related U.S. Application Data

[60] Provisional application No. 60/024,696, Sep. 6, 1996.

[51] Int. Cl.$^6$ .................................................. A61K 38/20
[52] U.S. Cl. ................................ 424/85.2; 514/2; 514/12
[58] Field of Search ............................... 424/85.2; 514/2, 514/12

[56] References Cited

U.S. PATENT DOCUMENTS

| | | |
|---|---|---|
| 5,188,827 | 2/1993 | Black . |
| 5,211,947 | 5/1993 | Brennan et al. . |
| 5,231,012 | 7/1993 | Mosmann et al. ................... 435/69.52 |

FOREIGN PATENT DOCUMENTS

| | | |
|---|---|---|
| 0374791 | 6/1990 | European Pat. Off. . |

OTHER PUBLICATIONS

Lissoni, et al.*Br. J. Cancer*, 1991, 64:956–958.
Hermus, et al., Arteriolscl. Thromb., 1992, 12(9):1036–1043.
Chensue, et al.*Clin. Exp. Immunol.*, 1994, 98395–400.
Darmani, et al.,*Mediators of Inflammaiton*, 1995, 4:25–30.
Querfeld, et al.,*J. of Lipid Research*, 1990, 31:1379–1386.
Stopeck, et al.,*J. of Biological Chemistry*, 1993, 268(23):17489–17494.
Krauss, et al. Endocrinology, 1990 127(3):1016–21.
Auerback, et al., *J. of Bilogical Chemistry*, 1989, 264(17):10264:10270.
Hamanaka, et al., *J. Of Bilogical Chemistry*, 1992, 267(19):13160–13165.
Grunfeld, et al.,*Endocrinology,*1990, 127(1):46–54.
Wilson, et al.,*J. of Clinical Oncology,*1989, 7(10):1573–1577.
Li, et al.,*J. Clin. Invest.*, 1995, 95:122–133.
Feingold, et al., Endocrinology, 1989, 125(1):267–264.

*Primary Examiner*—Garnette Draper
*Attorney, Agent, or Firm*—Cynthia L. Foulke

[57] ABSTRACT

A method for lowering the blood cholesterol levels in mammals and humans by administering IL-10 is disclosed. Preferred dosages and methods of administration are also disclosed.

27 Claims, 2 Drawing Sheets

METHOD FOR LOWERING CHOLESTEROL LEVELS WITH INTERLEUKIN-10

This application claims priority to U.S. provisional application number 60/024,696, filed Sep. 6, 1996.

BACKGROUND OF THE INVENTION

This invention relates to the lowering of serum cholesterol levels in mammals, especially humans. Elevated serum cholesterol levels are well recognized as a risk factor in heart disease. That is, the higher the serum cholesterol level, especially low-density lipoprotein cholesterol (LDL-C), the more likely a patient is to develop heart disease. After a patient has already developed heart disease and suffered a heart attack, the higher the serum cholesterol level, the more likely that patient will have another heart attack.

Hence there are well recognized benefits to lowering serum cholesterol levels.

There are many compounds available by prescription to lower serum cholesterol. Probably the most commonly used are the HMGCoA reductase inhibitors, e.g., lovastatin, prevastatin, simvastatin and fluvastatin.

While these compounds have some effect in lowering serum cholesterol, they do not always achieve lowering to a desired level, and they have undesirable side effects in some people, such as muscle necrosis and hyperkalemia.

The present invention lowers serum cholesterol with a well-tolerated active ingredient. Furthermore, in its preferred aspects, the present invention is believed to achieve significantly lower serum cholesterol levels than the HMG-CoA reductase inhibitors.

SUMMARY OF THE INVENTION

The present invention may be summarized as a method for lowering serum cholesterol in a mammal, especially in a human, by administering an effective amount of interleukin-10 (IL-10). Preferably, the IL-10 is administered to mammals diagnosed as having elevated blood serum cholesterol levels (hypercholesterolemia), or to those who have already developed atherosclerotic heart or vascular disease. Preferably, the mammals treated will be humans and the IL-10 will be recombinant human IL-10 (rhIL-10).

The presently preferred method of administration is by subcutaneous injection of from about 1 to 100 mcg/kg of patient's body weight. More preferably the IL-10 is administered daily for a period of a least 3 days in an amount of 1 to 15 mcg/kg.

DETAILED DESCRIPTION OF THE INVENTION

Figure 1:
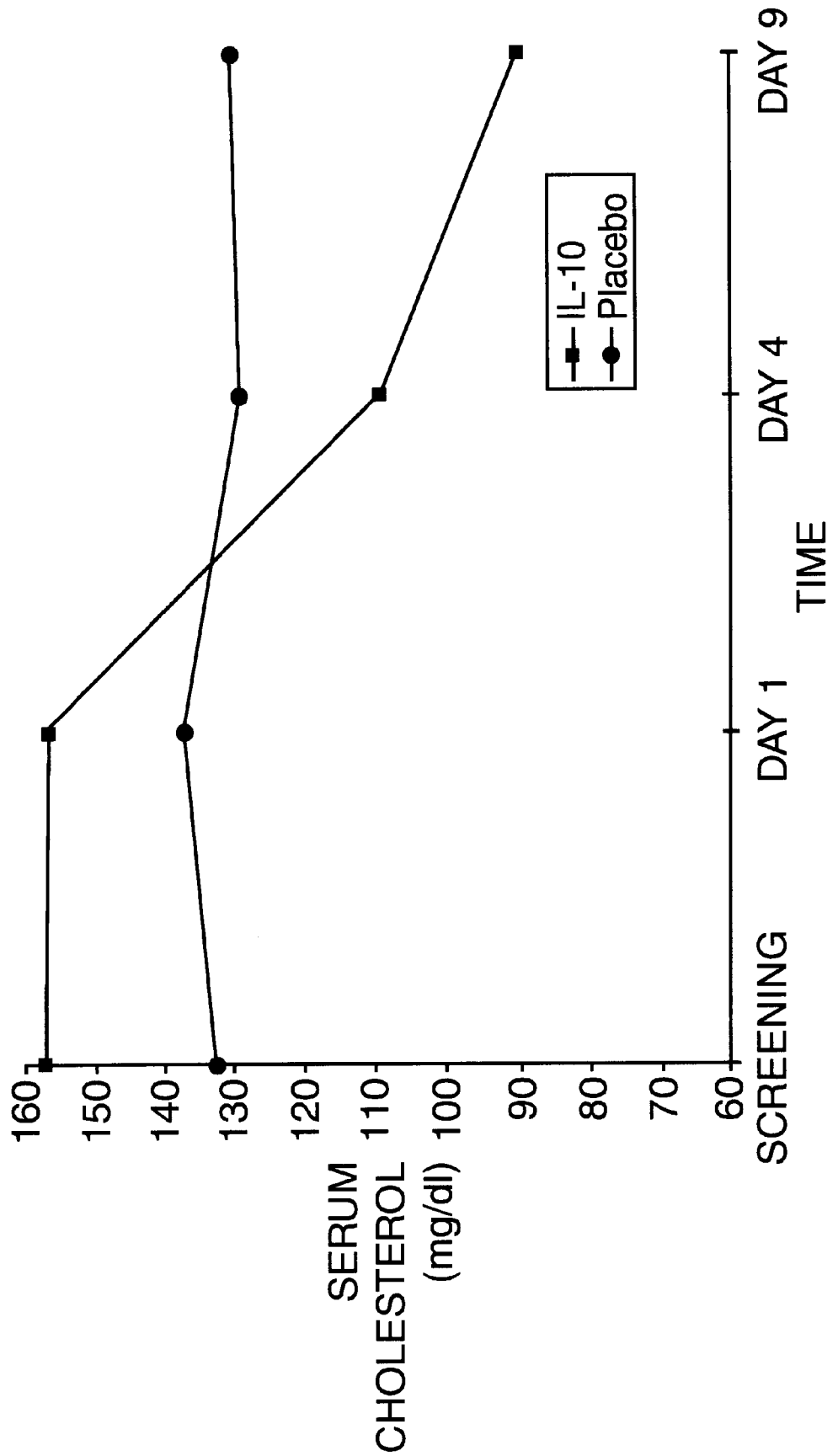
FIG. 1 illustrates average serum cholesterol levels for patients administered 8 mcg/kg rhIL-10 subcutaneously for 7 consecutive days and a control group receiving a placebo.

The invention provides a method for lowering blood cholesterol levels in mammals, e.g., mammals with hypercholesterolemia or normocholesterolemia, by administering a serum cholesterol lowering effective amount of IL-10. Elevated cholesterol levels can be associated with cardiovascular disease (e.g. atherosclerosis), cerebrovascular disease (stroke), and peripheral vascular disease.

As used herein, interleukin 10 or IL-10 is defined as a protein which (a) has an amino acid sequence substantially identical to a known sequence of mature (i.e., lacking a secretory leader sequence) IL-10 as disclosed in International Application Publication No. 91/003249, and (b) has biological activity that is common to native IL-10. For the purposes of this invention, both glycosylated (e.g., produced in eukaryotic cells such as yeast or CHO cells) and unglycosylated (e.g., chemically synthesized or produced in E. coli) IL-10 are equivalent and can be used interchangeably Also included are muteins and other analogs, including viral IL-10, which retain the biological activity of IL-10.

IL-10 suitable for use in the invention can be obtained from a number of sources. For example, it can be isolated from culture media of activated T-cells capable of secreting the protein. Additionally, the IL-10 or active fragments thereof can be chemically synthesized using standard techniques known in the art. See, e.g., Merrifield, 1986, Science 233:341–347 and Atherton et al., *Solid Phase Peptide Synthesis, A Practical Approach,* 1989, IRL Press, Oxford.

Preferably, the protein or polypeptide is obtained by recombinant techniques using isolated nucleic acids encoding the IL-10 polypeptide. General methods of molecular biology are described, e.g., by Sambrook et al., 1989, *Molecular Cloning, A Laboratory Manual,* 2d Ed., Cold Spring Harbor, New York and Ausubel et al. (eds). *Current Protocols in Molecular Biology,* Green/Wiley, N.Y. (1987 and periodic supplements). The appropriate sequences can be obtained using standard techniques from either genomic or cDNA libraries. DNA constructs encoding IL-10 may also be prepared synthetically by established standard methods, e.g., in an automatic DNA synthesizer, and then purified, annealed, ligated and cloned in suitable vectors. Atherton et al., 1989. Polymerase chain reaction (PCR) techniques can be used. See e.g., PCR Protocols: *A Guide to Methods and Applications,* 1990, Innis et al. (ed.), Academic Press, New York.

The DNA constructs may contain the entire native sequence of IL-10 or a homologue thereof. The term "homologue" is intended to indicate a natural variant of the DNA sequence encoding IL-10 or a variant or fragment produced by modification of the DNA sequence. Examples of suitable modifications of the DNA sequence are nucleotide substitutions which do not give rise to another amino acid sequence or nucleotide substitutions which do give rise to a different amino acid sequence and therefore, possibly, a different protein structure. Other examples of possible modifications are insertions of one or several nucleotides into the sequence, addition of one or several nucleotides at either end of the sequence, or deletion of one or several nucleotides at either end or within the sequence. Any homologous DNA sequence encoding a protein which exhibits IL-10 activity (e.g., with respect suppression of T cell proliferation or cholesterol lowering) similar to that of the naive protein is contemplated for use in the claimed invention.

The nucleotide sequences used to transfect the host cells can be modified, as described above, to yield IL-10 muteins and fragments with a variety of desired properties. Such modified IL-10 can vary from the naturally-occurring sequence at the primary level, e.g., by amino acid insertions, substitutions, deletions and fusions. Preferably, amino acid substitutions will be conservative; i.e., basic amino acid residues will be replaced with other basic amino acid residues, etc. These modifications can be used in a number of combinations to produce the final modified protein chain.

Amino acid sequence variants can be prepared with various objectives in mind, including increasing serum half-life, facilitating purification or preparation, improving therapeutic efficacy, and lessening the severity or occurrence of side effects during therapeutic use. The amino acid sequence variants are usually predetermined variants not found in nature, although others may be post-translational variants, e.g., glycosylation variants or proteins which are conjugated to polyethylene glycol (PEG), etc. Such variants can be used in this invention as long as they retain the biological activity of IL-10.

Preferably, human IL-10 is used for the treatment of humans, although viral or mouse IL-10, or IL-10 from some other mammalian species, could be used instead. Most preferably, the IL-10 used is recombinant human IL-10 (rhIL-10). Recombinant production of human IL-10 is described in U.S. Pat. No. 5,231,012. Preparation of human and mouse IL-10 has been described in International Application Publication No. WO 91/00349. The cloning and expression of viral IL-10 (BCRFI protein) from Epstein Barr virus has been disclosed by Moore et al. (Science 248:1230, 1990), and is described in EP 0 506 836.

Administration of IL-10 is preferably parenteral by intraperitoneal, intravenous, subcutaneous or intramuscular injection or infusion or by an other acceptable systemic method. Administration by subcutaneous injection is most preferred. Alternatively, the IL-10 may be administered by an implantable or injectable drug delivery system. See, e.g., Urquhart et al, 1984, *Ann Rev. Pharmacol. Toxicol* 24:199; Lewis, ed., 1981, *Controlled Release of Pesticides and Pharmaceuticals*, Plenum Press, New York, N.Y.: U.S. Pat. Nos. 3,773,919, and 3,270,960. Oral administration may also be carried out, using well known formulations which protect the IL-10 from gastrointestinal proteases.

Compositions useful for parenteral administration of such drugs are well known. See, e.g., Remington's Pharmaceutical Science, 11th Ed., 1990, Mack Publishing Co., Easton, Pa. For parenteral administration, the IL-10 is typically provided as a lyophilized powder, a preferred formula of which is given in the examples. The powder is reconstituted with sterile water for injection. The powder may contain minor amounts of additives such as substances that enhance isotonicity and chemical stability, e.g., buffers and preservatives. The IL-10 is preferably formulated in purified form substantially free of aggregates and other source proteins at a concentration in the range of about 25 mcg/ml to 2 mg/ml. Any of the well known carrier proteins such as human serum albumin can also be added if desired. Other injectable forms (solution, suspension, emulsion) in association with a pharmaceutical carrier may be used. Examples of such carriers are normal saline, Ringer's solution, dextrose solution, and Hank's solution. Non-aqueous carriers such as fixed oils and ethyl oleate may also be used.

IL-10 can also be delivered by standard gene therapy techniques, including e.g., direct DNA injection into tissues, the use of recombinant viral vectors or phospholipid and implantation of transfected cells. See, e.g., Rosenberg, 1992, *J. Clin. Oncol.* 10:180.

An effective amount of IL-10 is defined as any amount that will significantly lower the cholesterol level. A lowering of cholesterol by at least 5. percent is considered significant. More preferably the cholesterol level will be lowered by from 20 to 50 percent.

The amount, frequency and period of administration will vary depending upon factors such as the cholesterol level, (e.g. severity of the cholesterol elevation), age of the patient, nutrition, etc. Usually, the administration will be daily initially and it may continue periodically during the patient's lifetime. Dosage amount and frequency may be determined during initial screenings of cholesterol levels and the magnitude of the effect of IL-10 upon the lowering of the cholesterol levels. Dosage will be aimed to lower the cholesterol level to an acceptable level, which is currently believed to be less than about 200 milligrams per deciliter of blood serum. For patients with high risk (e.g. previous evidence of established coronary artery disease, smokers, low HDL-C (high density lipoprotein cholesterol) levels, diabetics, etc.,) more aggressive lowering of cholesterol, especially LDL-C is warranted.

The currently preferred dosage of IL-10 for practice of this invention is 1 to 100 mcg/kg, more preferably 1 to 15 mcg/kg administered daily for at least 3 days, more preferably for at least 7 days. Other dosing schedules, such as every other day, every third day, etc. are also believed effective. The currently preferred administration method is by subcutaneous injection. However when orally effective IL-10 formulations of IL-10 are perfected, oral administration would be more convenient.

To complement the cholesterol lowering effect of IL-10, it may be useful to administer it in conjunction with other pharmaceutically active compounds. For example, it can be combined with other cholesterol lowering agents [e.g., lovastatin (1,2,3,7,8,8a-hexahydro-3,7-dimethyl-8-[2-(tetrahydro4-hydroxy-6-oxo-2H-pyran-2-yl)-ethyl]-1-naphthalenyl 2-methylbutanoate, (U.S. Pat. No. 4,231,938)) available from Merck, Inc., Rahway, N.J. or other HMG-CoA reductase inhibitors; gemfribrozil (5-(2,5-dimethylphenoxy)- 2,2dimethylpentanoic acid), available from Parke-Davis, Inc., Ann Arbor, Mich.; pravastatin, which is available from Squibb, Inc., Princeton N.J.; niacin; nicotinic acid and its derivatives; cholestyramine; other anion exchange resins that bind to cholesterol; other cholesterol absorption inhibitors; or bile acids]. For lowering cholesterol levels that may be associated with acute manifestations of heart disease such as myocardial infarction, IL-10 can be administered in conjunction with thrombolytic agents [e.g., tissue plasminogen activators (tPAs) (for example, those disclosed in U.S. Pat. Nos. 4,370,417, 4,752, 603; U.K. Patent No. 2,119,804; PCT Patent Application Nos. 87/05934, 87/04722, 84/01786; Australian Patent Application No. 55514/86; EPO Patent Application Nos. 227,462, 234,051, 238,304, and 174,835, and the tPA is commercially available from Genentech, Inc., South San Francisco, Calif.); eminase (available from Beecham Inc., Bristol, Tenn., and Upjohn Corporation, Kalamazoo, Mich.); and streptokinase (for example, the materials disclosed in European Patent Application Nos. 248,227, 28,489; and the streptokinase commercially available from Burroughs-Wellcome, Inc., Research Triangle, N.C.)] or combinations of such thrombolytic agents (for example, see European Patent Application Nos. 91,240 and 28,489 for streptokinase/tPA complexes). These references are hereby incorporated by reference to illustrate examples of other cholesterol lowering agents and thrombolytic agents that can be used in combination with IL-10 in certain embodiments of the present invention. The specific cholesterol lowering agents and thrombolytic agents mentioned above are merely examples of such agents known to those skilled in the art that can be used in the practice of the present invention. It is believed that administering IL-10 in combination with another cholesterol-lowering agent may allow use of significantly less of the other agent, thereby eliminating or reducing the other agent's undesirable side effects.

Administration of the dose can be intravenous, nasal, parenteral, oral, subcutaneous, intramuscular, topical, transdermal or any other acceptable method. The IL-10 could be administered in any number of conventional dosage forms. Parenteral preparations include sterile solutions or suspensions. Inhalation administration can be in the form of a nasal or oral spray, or by insufflation. Topical dosage forms can be creams, ointments, lotions, transdermal devices (e.g., of the conventional reservoir or matrix patch type or iontophoresis) and the like.

The formulations and pharmaceutical compositions contemplated by the above dosage forms can be prepared with conventional pharmaceutically acceptable excipients and additives, using conventional techniques.

Preferably the IL-10 is administered via the subcutaneous route. The solutions to be administered may be reconstituted from lyophilized powders and they may additionally contain preservatives, buffers, dispersants, etc. Preferably, IL-10 is reconstituted with a medium normally utilized for intravenous injection, e.g., preservative-free sterile water. The maximum concentration of IL-10 preferably should not exceed 2000 micrograms per milliliter. Administration may be accomplished by continuous intravenous or subcutaneous infusion or by intravenous injection. For continuous infusion, the daily dose can be added to normal saline or other solution and the solution infused by mechanical pump or by gravity.

The following examples illustrate the effect of administration of human recombinant IL-10 (rhIL-10) on the serum cholesterol levels in healthy human volunteers.

EXAMPLES

Example 1: Daily Dosing for Seven Days

A group of patients having an initial serum cholesterol level between 150 and 160 mg/dl were dosed daily with 8 mcg of IL-10 per kg of body weight for 7 days. The IL-10 was administered by subcutaneous injection. The IL-10 was initially furnished as a lyophilized powder prepared from the following formulation

| Ingredient | mg/vial* |
|---|---|
| rhIL-10 | 0.8 |
| Sodium Citrate Dihydrate, USP/Ph. Eur | 3 |
| Sucrose, NF/Ph. Eur | 50 |
| Glycine, USP/Ph. Eur | 10 |
| Water for Injection, USP | 1.0 ml** |

*upon reconstitution the amount in 1.0 ml
**Sublimed during lyophilization

Each vial of lyophilized powder was reconstituted with 1.0 ml of sterile water for injection.

Figure 2:
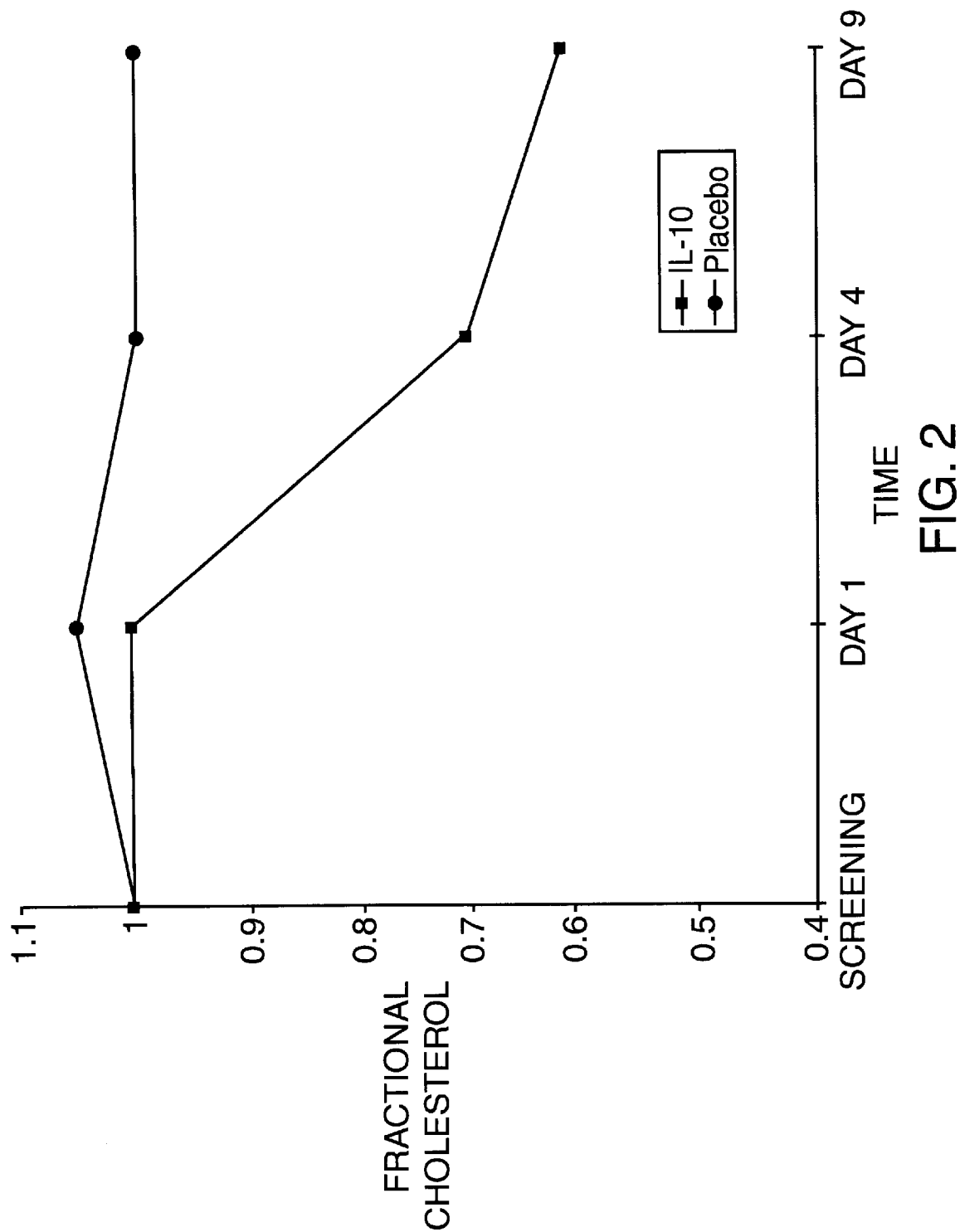
FIG. 2 illustrates the same data as FIG. 1 expressed as fractional cholesterol levels with the initial screening level equal to 1.

The results are shown in FIGS. 1 and 2.

A second group of patients having an average initial serum cholesterol level of between 130 and 140 mg/dl were injected with a placebo with the same regimen as the first group, except that the injected composition contained no IL-10. The results of this control experiment are also illustrated in FIGS. 1 and 2. It is immediately evident that IL-10 causes a rapid and very significant drop in serum cholesterol levels. Future experiments are planned to determine which type of cholesterol—LDL cholesterol (the so called bad cholesterol) or HDL cholesterol (the so called good cholesterol)—is most affected by IL-10. Future experiments should also determine the duration of the drop in cholesterol levels, and whether follow-up cholesterol measurements and further dosing with IL-10 are necessary

Example 2: Effect of a Single Dose of IL-10

Randomized, third-party blind, rising single-dose, placebo-controlled experiments were performed with the following dosages:

placebo (18 participants)

1, 2.5, 5, 10, 25, and 50 mcg/kg of IL-10 (6 participants at each dosage level). The results are shown in the following tables:

| Group | Baseline | 2 hours | 24 hours | 48 hours |
|---|---|---|---|---|
| Percent of Baseline (pretreatment) Cholesterol concentrations | | | | |
| placebo | 100 | 96 | 95 | 100 |
| 1 mcg/ml | 100 | 94 | 91 | 98 |
| 2.5 mcg/ml | 100 | 98 | 94 | 100 |
| 5 mcg/ml | 100 | 91 | 85 | 88 |
| 10 mcg/ml | 100 | 91 | 77 | 82 |
| 25 mcg/ml | 100 | 97 | 83 | 85 |
| 50 mcg/ml | 100 | 97 | 86 | 85 |
| Cholesterol Concentrations by Treatment (mg/dl) | | | | |
| placebo | 160 | 155 | 153 | 160 |
| 1 mcg/ml | 177 | 167 | 162 | 175 |
| 2.5 mcg/ml | 175 | 171 | 164 | 175 |
| 5 mcg/ml | 200 | 181 | 170 | 175 |
| 10 mcg/ml | 170 | 155 | 131 | 139 |
| 25 mcg/ml | 185 | 178 | 152 | 156 |
| 50 mcg/ml | 196 | 191 | 168 | 167 |
| Change from Baseline (pretreatment) Cholesterol Concentrations (mg/dl) | | | | |
| placebo | 0 | −5 | −7 | 0 |
| 1 mcg/ml | 0 | −10 | −15 | −2 |
| 2.5 mcg/ml | 0 | −4 | −11 | 1 |
| 5 mcg/ml | 0 | −18 | −30 | −25 |
| 10 mcg/ml | 0 | −15 | −39 | −31 |
| 25 mcg/ml | 0 | −6 | −33 | −29 |
| 50 mcg/ml | 0 | −5 | −28 | −29 |

Based on the above, it is clear that IL-10 is has the surprising effect of significantly lowering serum cholesterol levels in human patients.

I claim:

1. A method for lowering the blood serum cholesterol level in a mammal comprising administering to said mammal a serum cholesterol lowering effective amount of IL-10.

2. The method of claim 1 wherein said mammal is a human.

3. The method of claim 2 wherein said interleukin 10 is administered in an amount of about 1 to 100 micrograms per kilogram of body weight per dose.

4. The method of claim 3 wherein said dose is administered daily for at least 3 days.

5. The method of claim 4 wherein said dose is administered daily for at least 7 days.

6. The method of claim 5 wherein the daily dose is from 1 to 15 micrograms per kilogram of body weight.

7. The method of claim 1 wherein said interleukin 10 is recombinant human interleukin 10.

8. The method of claim 2 wherein said interleukin 10 is recombinant human interleukin 10.

9. The method of claim 3 wherein said interleukin 10 is recombinant human interleukin 10.

10. The method of claim 4 wherein said interleukin 10 is recombinant human interleukin 10.

11. The method of claim 5 wherein said interleukin 10 is recombinant human interleukin 10.

12. The method of claim 6 wherein said interleukin 10 is recombinant human interleukin 10.

13. The method of claim 1 wherein interleukin 10 is administered by subcutaneous injection.

14. The method of claim 2 wherein the interleukin 10 is administered by subcutaneous injection.

15. The method of claim 3 wherein the interleukin 10 is administered by subcutaneous injection.

16. The method of claim 4 wherein the interleukin 10 is administered by subcutaneous injection.

17. The method of claim 5 wherein the interleukin 10 is administered by subcutaneous injection.

18. The method of claim 6 wherein the interleukin 10 is administered by subcutaneous injection.

19. The method of claim 7 wherein the interleukin 10 is administered by subcutaneous injection.

20. The method of claim 8 wherein the interleukin 10 is administered by subcutaneous injection.

21. The method of claim 9 wherein the interleukin 10 is administered by subcutaneous injection.

22. The method of claim 10 wherein the interleukin 10 is administered by subcutaneous injection.

23. The method of claim 11 wherein the interleukin 10 is administered by subcutaneous injection.

24. The method of claim 12 wherein the interleukin 10 is administered by subcutaneous injection.

25. The method of claim 1 wherein the interleukin 10 is administered in combination with an agent selected from the group consisting of a cholesterol lowering agent and a thrombolytic agent.

26. The method of claim 1 wherein the interleukin 10 is administered every other day.

27. The method of claim 1 wherein the interleukin 10 is administered every third day.

* * * * *